(12) United States Patent
Okoniewski (10) Patent No.: US 8,926,504 B2
(45) Date of Patent: Jan. 6, 2015

(54) ACCESS ASSEMBLY

(75) Inventor: Gregory Okoniewski, North Haven, CT (US)

(73) Assignee: Covidien LP, Mansfield, MA (US)

(*) Notice: Subject to any disclaimer, the term of this patent is extended or adjusted under 35 U.S.C. 154(b) by 373 days.

(21) Appl. No.: 13/193,652

(22) Filed: Jul. 29, 2011

(65) Prior Publication Data

US 2012/0083660 A1 Apr. 5, 2012

Related U.S. Application Data

(60) Provisional application No. 61/388,626, filed on Oct. 1, 2010.

(51) Int. Cl.
*A61B 1/00* (2006.01)
*A61B 17/34* (2006.01)
*A61B 17/00* (2006.01)

(52) U.S. Cl.
CPC ... *A61B 17/3423* (2013.01); *A61B 2017/00557* (2013.01); *A61B 2017/3443* (2013.01); *A61B 2017/3466* (2013.01); *A61B 2017/3445* (2013.01)
USPC ........................................ 600/184

(58) Field of Classification Search
USPC .......... 220/426; 600/185, 201, 184, 203–208; 606/108, 191
See application file for complete search history.

(56) References Cited

U.S. PATENT DOCUMENTS

| 5,366,478 | A | 11/1994 | Brinkerhoff et al. |
| 5,803,921 | A | 9/1998 | Bonadio |
| 5,906,577 | A | 5/1999 | Beane et al. |
| 5,964,781 | A | 10/1999 | Mollenauer et al. |
| 6,033,428 | A | 3/2000 | Sardella |
| 6,440,063 | B1 | 8/2002 | Beane et al. |
| 6,454,783 | B1 | 9/2002 | Piskun |
| 6,972,026 | B1 | 12/2005 | Caldwell et al. |
| 7,850,600 | B1 | 12/2010 | Piskun |
| 2005/0090716 | A1* | 4/2005 | Bonadio et al. ............... 600/207 |
| 2008/0027476 | A1 | 1/2008 | Piskun |
| 2009/0221966 | A1 | 9/2009 | Richard |
| 2010/0100043 | A1 | 4/2010 | Racenet |
| 2010/0249524 | A1 | 9/2010 | Ransden et al. |
| 2011/0082341 | A1 | 4/2011 | Kleyman et al. |
| 2011/0166423 | A1 | 7/2011 | Farascioni et al. |

FOREIGN PATENT DOCUMENTS

| EP | 2 044 889 | 4/2009 |
| EP | 2 289 438 | 3/2011 |
| EP | 2 343 019 | 7/2011 |
| WO | WO 00/54675 | 9/2000 |

OTHER PUBLICATIONS

European Search Report from EP Application No. EP 12 15 2164 mailed Apr. 19, 2012.
European Search Report from EP Application No. EP 12 15 2128 mailed Apr. 20, 2012.

* cited by examiner

Primary Examiner — Thomas McEvoy (57) ABSTRACT

An access assembly includes a body portion defining a longitudinal axis and having at least one lumen defined therethrough. The at least one lumen is configured for passage of a surgical instrument therethrough. An outer sleeve is disposed about the body portion to define a chamber therebetween. The chamber is selectively inflatable from a deflated condition, for positioning the access assembly within an opening in tissue, and an inflated condition, for retaining the access assembly within the opening in tissue in sealing relation therewith.

8 Claims, 9 Drawing Sheets

ACCESS ASSEMBLY

CROSS-REFERENCE TO RELATED APPLICATIONS

The present application claims the benefit of and priority to U.S. Provisional Application No. 61/388,626 filed on Oct. 1, 2010, the entire contents of which are incorporated by reference herein.

BACKGROUND

1. Technical Field

The present disclosure relates to access assemblies and, more particularly, to inflatable, multi-lumen access assemblies for use in single incision surgical procedures.

2. Background of Related Art

In an effort to reduce trauma and recovery time, many surgical procedures are performed through small openings in the skin, such as an incision or a natural body orifice. These procedures, referred to as endoscopic surgical procedures, include laparoscopic procedures, which are generally performed within a patient's abdomen, and thoracic procedures, which are generally performed with a patient's chest cavity. Throughout the present disclosure, the term "minimally invasive" should be understood to encompass any and all such procedures.

During a typical minimally invasive procedure, the clinician creates an opening through the patient's body wall using an obturator or trocar and thereafter positions an access port within the opening. The access port typically includes an access sleeve that is configured and dimensioned to receive one or more surgical instruments to facilitate positioning within an internal work site adjacent the tissue that is the subject of the procedure. In some minimally invasive procedures, prior to the introduction of surgical instrumentation into the patient's body, insufflation gasses are used to enlarge the area surround the target surgical site to create a larger and more accessible work area. Accordingly, the maintenance of a substantially fluid-tight seal is desirable during such procedures so as to prevent the escape of the insufflation gasses and the deflation or collapse of the enlarged surgical site.

SUMMARY

In accordance with one embodiment of the present disclosure, an access assembly is provided. The access assembly includes a body portion defining a longitudinal axis and having one or more lumens defined therethrough. Each lumen is configured for passage of a surgical instrument therethrough. The access assembly further includes an outer sleeve disposed about the body portion to define a chamber therebetween. The chamber is selectively inflatable from a deflated condition to an inflated condition. The access assembly is configured such that, in the deflated condition, the access assembly is positionable within an opening in tissue and, such that, in the inflated condition, the access assembly is retained within the opening in tissue in sealing relation therewith.

In one embodiment, the body portion of the access assembly includes one or more slits defined therein and extending partially longitudinally therethrough. Alternatively, the body portion may include one or more indentations defined within an outer surface thereof.

In another embodiment, a valve is disposed on the outer sleeve in fluid communication with the chamber. The valve is configured to selectively permit the introduction of inflation fluids into the chamber for inflating the chamber or removal of inflation fluids for deflating the chamber.

In still another embodiment, the access assembly is formed as a single component. More specifically, a free end of the outer sleeve may be sealingly engaged to the body portion to define the chamber therebetween during assembly of the access assembly.

In yet another embodiment, the access assembly defines a generally hourglass-shaped configuration.

The chamber may be configured for receipt of an inflation fluid, e.g., air, water, etc., therein. Alternatively, or additionally, the chamber may be at least partially filled with a compressible material.

A method for providing access to a surgical site is also provided in accordance with the present disclosure. The method includes providing an access assembly according to any of the embodiments discussed above. The method further includes deflating the access assembly, inserting the access assembly into an opening in tissue, and inflating the access assembly such that the access assembly is retained within the opening in tissue in substantially fluid-tight relation therewith. Thereafter, one or more surgical instruments may be inserted through the lumen(s) of the access assembly to perform a surgical procedure within an internal surgical site.

In accordance with the present disclosure, a method of manufacturing an access assembly, e.g., any of the access assemblies discussed above, is also provided. The method includes forming a single component defining a longitudinal axis, the single component having a body portion disposed about the longitudinal axis and an outer sleeve extending distally from the body portion. The method further includes folding a free end of the outer sleeve radially over an outer surface of the outer sleeve, translating the free end of the outer sleeve proximally to a position adjacent a proximal end of the body portion, and sealingly engaging the free end of the outer sleeve to the proximal end of the body portion to define an inflatable chamber radially disposed between the outer sleeve and the body portion.

In one embodiment, the body portion of the single component is formed with at least one lumen extending longitudinally therethrough.

In another embodiment, a valve is positioned within the outer sleeve. The valve is configured to permit selective inflation (and/or deflation) of the inflatable chamber.

In still another embodiment, the free end of the outer sleeve is sealingly bonded, or, alternatively, is sealingly welded, to the proximal end of the body portion

BRIEF DESCRIPTION OF THE DRAWINGS

Various embodiments of the presently disclosed access ports are described herein with reference to the drawings, wherein.

DETAILED DESCRIPTION

Embodiments of the present disclosure are described in detail with reference to the drawing figures wherein like reference numerals identify similar or identical elements. As used herein, the term "distal" refers to the portion that is being described which is further from the clinician, while the term "proximal" refers to the portion that is being described which is closer to the clinician.

Turning now to FIGS. 1-6, one embodiment of an inflatable access assembly is shown generally identified by reference numeral 100. Access assembly 100 may be formed of various materials such as, for example, silicone, thermoplastic elastomers (TPE), rubber, foam, gel, etc. As will be described in greater detail below, access assembly 100 is selectively inflatable from a deflated condition, permitting access assembly 100 to be inserted through an opening in tissue and manipulated into position, to an inflated condition, wherein, once positioned within an opening in tissue and inflated, access assembly 100 creates a substantially fluid-tight seal within the opening in tissue to inhibit passage of fluids between the internal body cavity and the external environment and wherein access assembly 100 is maintained in position within the opening in tissue. Further, access assembly 100 may be selectively inflated to various inflation levels such that access assembly 100 may be sealingly and/or fixedly positioned within openings in tissue having various sizes, shapes, and configurations.

With continued reference to FIGS. 1-6, access assembly 100 defines a longitudinal axis "X-X" and includes a generally cylindrical body portion 110 disposed about longitudinal axis "X-X" and an outer sleeve 120 radially disposed about body portion 110. Body portion 110 includes a proximal rim 112 and a distal rim 114 and has sufficient length to extend through an opening in tissue. In other words, body portion 110 is configured to be positioned within an opening in tissue such that proximal rim 112 of body portion 110 is disposed on a proximal, or external surface of tissue and such that distal rim 114 is disposed on a distal, or internal surface of tissue. As can be appreciated, since the thickness of tissue depends at least on the body composition of the patient and the anatomical location through which the underlying cavity is being accessed, body portion 110 of access assembly 100 may define various lengths and/or sizes according to the characteristics of the patient and/or the specific procedure to be performed.

Figure 6:
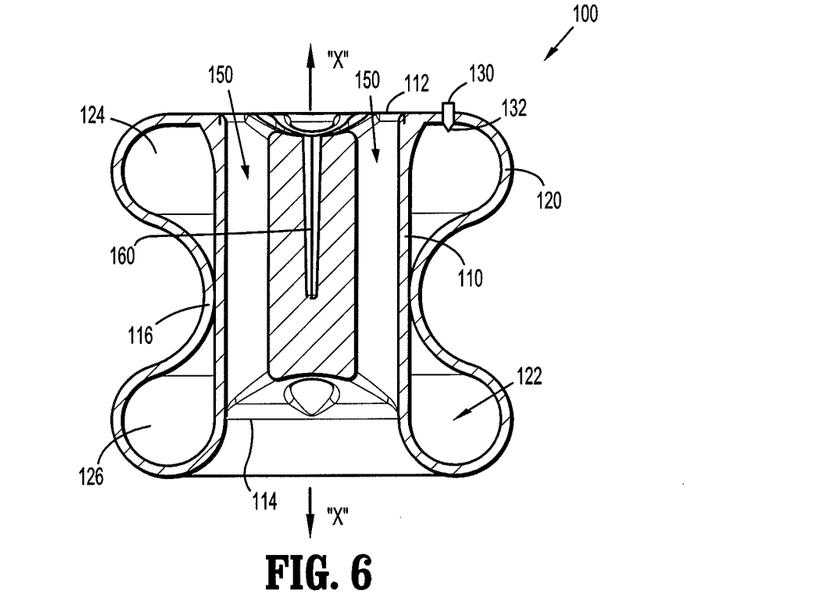
FIG. 6 is a longitudinal cross-sectional view of the access assembly of FIG. 1 taken along section line 6-6 of FIG. 5.

Continuing with reference to FIGS. 1-6, and in particular to FIG. 6, outer sleeve 120 of access assembly 100 extends from each of the proximal and distal rims 112, 114, respectively, of body portion 110 to define a chamber 122 that is radially disposed, relative to longitudinal axis "X-X," between body portion 110 and outer sleeve 120. Chamber 122 extends between proximal rim 112 and distal rim 114 of body portion 110 along a substantial length of access assembly 100. As will be described in greater detail below, body portion 110 and outer sleeve 120 are sealingly engaged to one another, allowing chamber 122 to retain an inflation fluid therein.

Figure 4:
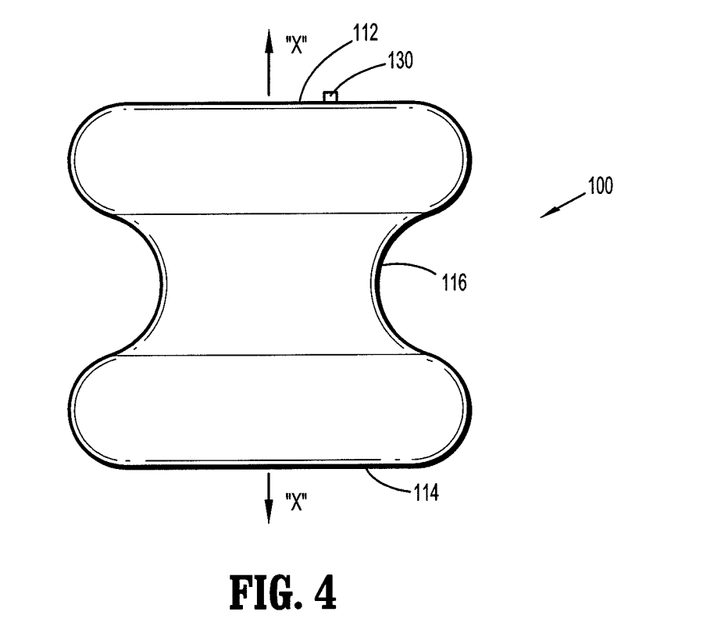
FIG. 4 is a side view of the access assembly of FIG. 1.
Figure 5:
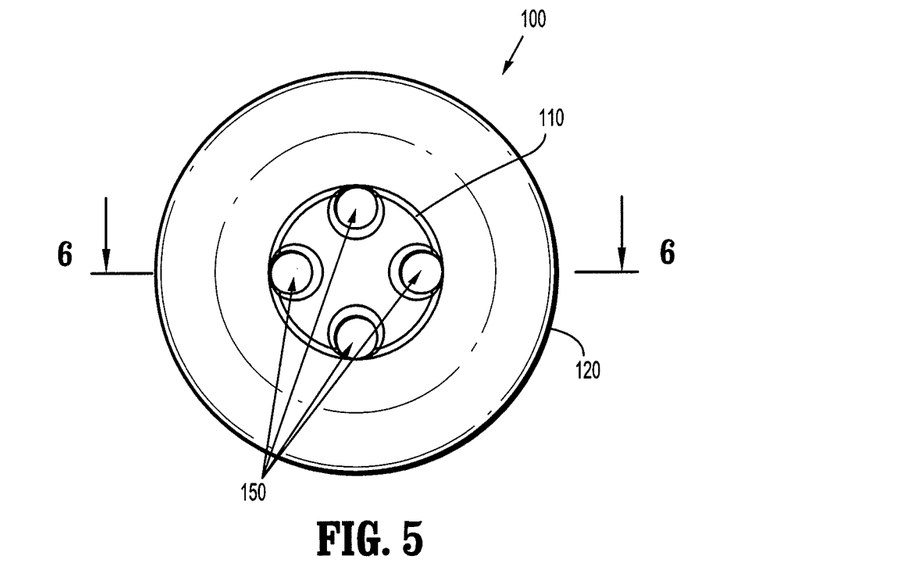
FIG. 5 is a bottom view of the access assembly of FIG. 1.

As best shown in FIGS. 4 and 6, the hourglass-shaped configuration of outer sleeve 120 of access assembly 100 divides chamber 122 into proximal and distal ring-like sections 124, 126, respectively. Proximal and distal sections 124, 126, respectively, of chamber 122 may be in fluid communication with one another such that inflation fluid may pass therebetween, or may be sealed from one another during the manufacturing process, e.g., outer sleeve 120 may be sealingly engaged to body portion 110 circumferentially about a waist 116 of access assembly 100, such that either or both of proximal and distal sections 124, 126, respectively, of chamber 122 may be selectively inflated independently of one another. Further, proximal and distal ring sections 124, 126 of chamber 122 may be equally sized, or one of proximal and distal sections 124, 126, respectively, of chamber 122 may be relatively larger (or smaller) than the other, e.g., the waist 116 of access assembly 100 may be disposed closer to proximal rim 112 or, alternatively, closer to distal rim 114. Further, the portion of outer sleeve 120 disposed adjacent to waist 116 of access assembly 100 may be thicker, stiffer, or otherwise configured such that, when inflated, proximal and distal ring-like sections 124, 126, respectively, of chamber 122 are more easily inflated relative to waist 116 to assume the hourglass-shaped configuration of access assembly 100. As can be appreciated, such a configuration reduces the pressure applied to tissue during inflation of access assembly 100. Ultimately, however, the specific configuration of proximal and distal sections 124, 126, respectively, of chamber 122 may depend on the body composition of the patient, the anatomical location through which the opening in tissue is formed, and/or the surgical procedure to be performed.

Figure 1:
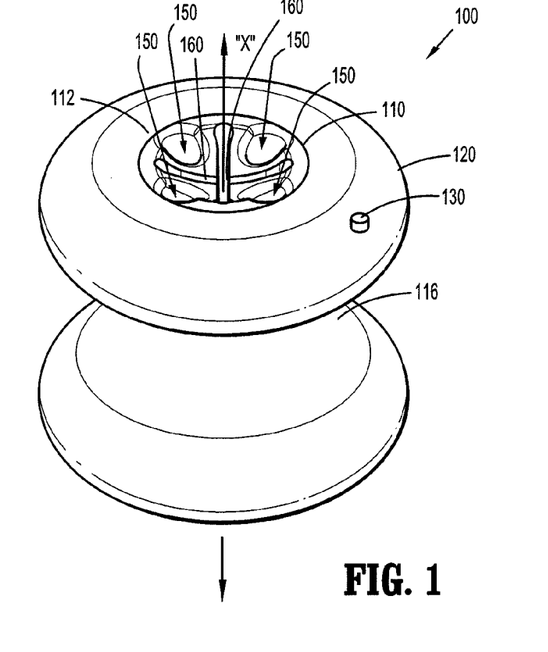
FIG. 1 is a perspective view of a proximal end of one embodiment of an access assembly in accordance with the present disclosure.
Figure 2:
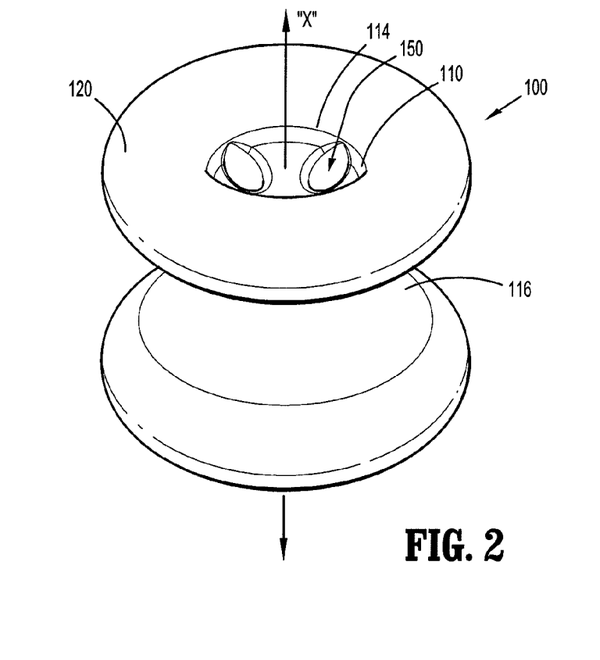
FIG. 2 is a perspective view of a distal end of the access assembly of FIG. 1.
Figure 3:
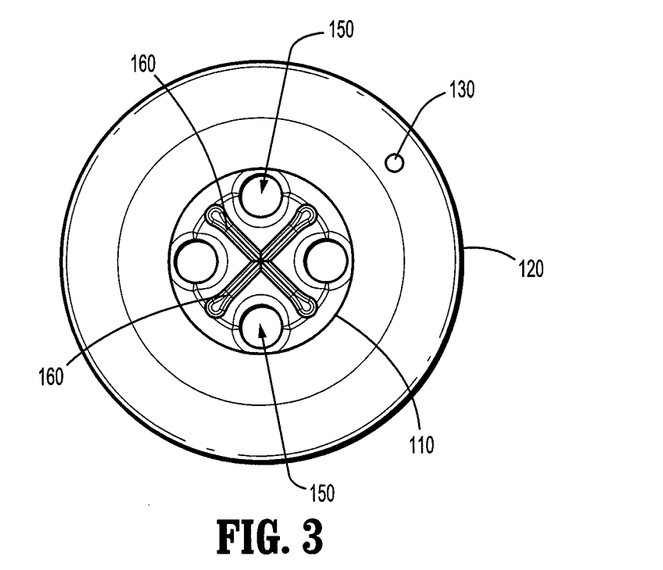
FIG. 3 is a top view of the access assembly of FIG. 1.

As best shown in FIGS. 1 and 6, access assembly 100 includes a valve 130 for coupling an inflation source (not shown) to chamber 122 to inflate (and/or deflate) chamber 122. For example, valve 130 may include a one-way seal member 132 (FIG. 6) that permits passage of inflation fluid, e.g., air, water, etc., therethrough, but inhibits the inflation fluid from escaping chamber 122. More specifically, a nozzle (not shown) of an inflation source (not shown) may be inserted through one-way seal member 132 of valve 130 to supply inflation fluid to chamber 122. In such an embodiment, upon removal of the inflation source (not shown), one-way seal member 132 is automatically returned to a closed position to inhibit the inflation fluid from escaping chamber 122. Alternatively, valve 130 may be configured as a check valve (not shown), or as any other suitable valve that permits passage of inflation fluid therethrough but inhibits the inflation fluid from escaping chamber 122. As can be appreciated, chamber 122 may also be deflated through valve 130. For example, a vacuum source (not shown) may be coupled to valve 130 to suction out the inflation fluid from chamber 122, or, alternatively, valve 130 may simply be transitioned to an open state to permit the inflation fluid to escape from chamber 122, e.g., upon compression of access assembly 100. An independent release valve (not shown) or other release mechanism (not shown) for deflating access assembly 100 may also be provided.

It is also envisioned that chamber 122 be filled (at least partially) with a compressible material (not explicitly shown). Suitable compressible materials include silicone, thermoplastic elastomers (TPE), rubber, foam, gel and other compressible materials that are capable of being resiliently compressed to facilitate insertion of access assembly 100 into an incision. It is envisioned that the entire chamber 122, e.g., both the proximal and distal sections 124, 126, respectively, may be filled with compressible material, or that only one of proximal and distal sections 124, 126, respectively, be filled with compressible material, while the other section 124, 126 of chamber 122 is configured, as discussed above, to be inflated via an inflation source (not shown).

Referring once again to FIGS. 1-6, body portion 110 of access assembly 100 extends longitudinally through access assembly 100 about longitudinal axis "X-X" and includes a plurality, e.g., four (4), longitudinally extending lumens 150 defined therethrough. Lumens 150 of access assembly 100 extend completely through access assembly 100 and define substantially similar sizes and shapes for receiving surgical instrumentation "S" (FIGS. 17-18) therethrough, although one or more lumens 150 may have a different size and/or shape for receiving surgical instrumentation "S" (FIGS. 17-18) of different configurations. Further, lumens 150 may be configured to be expandable, due to the flexible configuration of body portion 110 of access assembly 100, such that lumens 150 may receive surgical instrumentation "S" (FIGS. 17-18) of varying size therethrough in sealing relation therewith. Further, lumens 150 may be biased toward a collapsed, or closed condition, wherein the openings extending through lumens 150 are closed, or sealed-off, inhibiting fluids from passing therethrough. Such a configuration helps maintain the internal surgical site in an insufflated state in the absence of surgical instrumentation "S" (FIGS. 17-18) inserted through each of lumens 150. Lumens 150 may also include a protective lining (not shown) to prevent tearing of access assembly 100 as surgical instrumentation "S" (FIGS. 17-18) is inserted therethrough and manipulated therein and/or may be coated with a lubricant to assist in insertion and/or removal of surgical instrumentation "S" (FIGS. 17-18) from access assembly 100.

Continuing with reference to FIGS. 1-6, body portion 110 of access assembly 100 further includes a pair of slits 160 defined therein, although greater or fewer than two slits 160 are also contemplated. Slits 160 extend longitudinally partially through body portion 110 of access assembly 100 and are positioned perpendicularly relative to one another. Slits 160 intersect one another on longitudinal axis "X-X" to define four quadrants; each quadrant including one of lumens 150. As can be appreciated, in embodiments where only three lumens 150 are provided, three slits 160 may be defined through body portion 110 at angles of 120 degrees relative to one another to define three sections, each containing a lumen 150, although any suitable number and/or configuration of slits 160 and lumens 150 is contemplated. Further, the sections defined by slits 160 may define unequal areas and/or may include multiple lumens 150 (or no lumens). Additionally, slits 160 may be positioned off-center relative to longitudinal axis "X-X," e.g., slits 160 may not intersect on longitudinal axis "X-X."

As can be appreciated, slits 160 help increase the flexibility of access assembly 100 and also allow for increased maneuverability of surgical instrumentation "S" (FIGS. 17-18) inserted through lumens 150. Further, by dividing body portion 110 into quadrants, lumens 150 are capable of being flexed, or moved independently, or less dependently, of one another. In other words, slits 160 not only permit increased lateral manipulation of surgical instrumentation "S" (FIGS. 17-18) inserted through lumens 150 but also permit manipulation of surgical instrumentation "S" (FIGS. 17-18) inserted through one of lumens 150 without substantially effecting the positioning of other surgical instrumentation "S" (FIGS. 17-18) inserted through the other lumens 150. To this end, the longitudinal depth of slits 160 may be selected according to the desired flexibility of body portion 110 of access assembly 100 and/or the desired independence between lumens 150. For example, where it is desired to provide a greater amount of lateral manipulation and/or greater independence between lumens 150, slits 160 may extend almost completely through body portion 110 of access assembly 100. On the other hand, where less flexibility is desired, slits 160 may only extend a relatively small distance longitudinally through access assembly 100.

Figure 7:
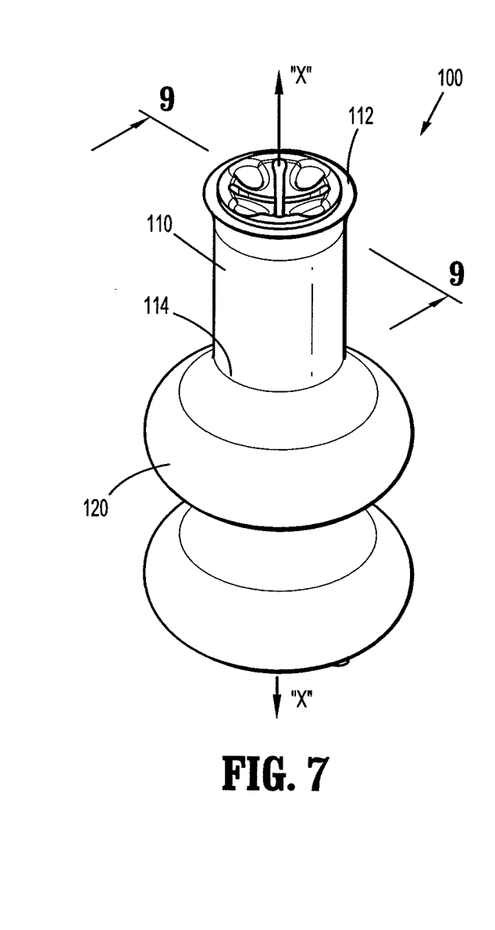
FIG. 7 is a perspective view of the proximal end of the access assembly of FIG. 1 prior to assembly.
Figure 8:
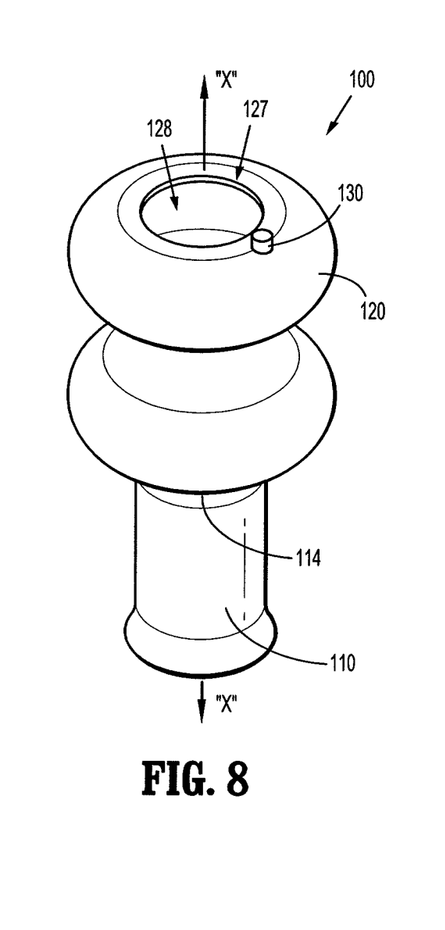
FIG. 8 is a perspective view of the distal end of the access assembly of FIG. 1 prior to assembly.

Referring now to FIGS. 7-11, the manufacture and assembly of access assembly 100 will be described. Access assembly 100 is manufactured as a single component, or piece with body portion 110 and outer sleeve 120 monolithically formed with one another at distal rim 114 of body portion 110. Prior to assembly, as best shown in FIGS. 7-8, body portion 110 is axially spaced from outer sleeve 120, e.g., body portion 110 extends proximally from outer sleeve 120 along longitudinal axis "X-X," such that free end 127 of outer sleeve 120 is disposed at one end of access assembly 100 and such that proximal rim 112 of body portion 110 is disposed at the opposite end of access assembly 100.

Figures 9, 10:
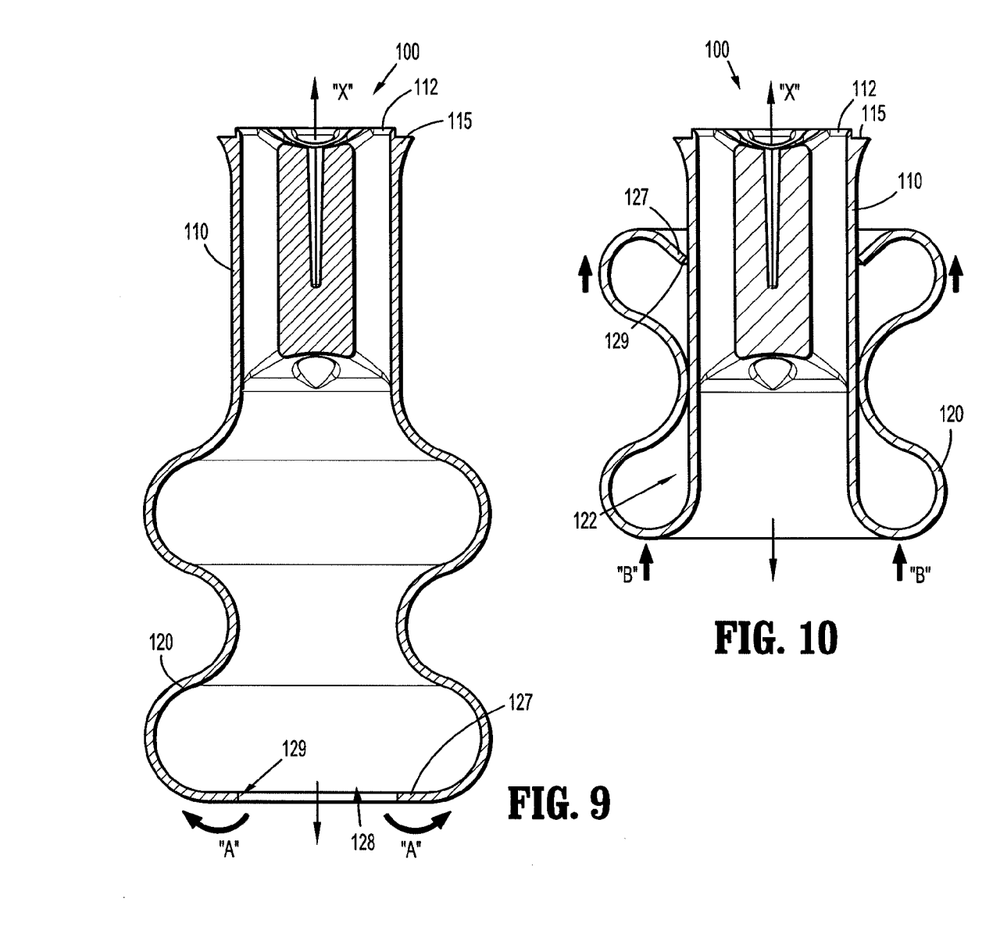
FIG. 9 is a longitudinal cross-sectional view of the access assembly of FIG. 1 prior to assembly taken along section line 9-9 of FIG. 7.
FIG. 10 is a longitudinal cross-sectional view of the access assembly of FIG. 1 during assembly.
Figure 11:
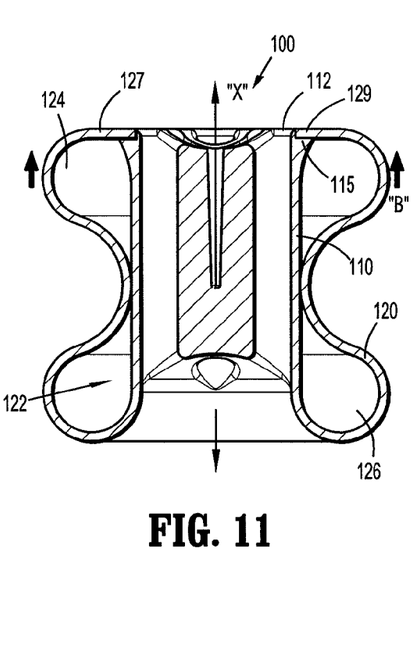
FIG. 11 is a longitudinal cross-sectional view of the access assembly of FIG. 1 as assembled.

Turning now to FIGS. 9-11, in order to assembly access assembly 100, free end 127 of outer sleeve 120 is turned radially outwardly, as indicated by arrows "A" in FIG. 9, and is translated proximally relative to body portion 110, as indicated by arrows "B" (FIGS. 10-11). As free end 127 of outer sleeve 120 is translated proximally, outer sleeve 120 is increasingly turned inside-out and moved proximally. More specifically, free end 127 of outer sleeve 120 includes an aperture 128 defined therethrough such that free end 127 of outer sleeve 120 may be moved proximally relative to body portion 110 and, at the same time, outer sleeve 120 may pass through aperture 128 of free end 127 and thereafter turn radially outwardly to permit further advancement of free end 127.

As best shown in FIGS. 10-11, free end 127 of sleeve 120 of access assembly 100 is moved further proximally relative to body portion 110 of access assembly 100 until outer sleeve 120 has substantially completely passed through aperture 128 defined within free end 127 of outer sleeve 120. More specifically, sleeve 120 is moved proximally until sleeve 120 is disposed about body portion 110 of access assembly 100. In this position, inner circumferential surface 129 defined by aperture 128 of free end 127 of outer sleeve 120 is bonded, welded, or otherwise sealingly engaged to proximal annular shelf 115 of body portion 110. As such, with inner circumferential surface 129 of aperture 128 of free end 127 of outer sleeve 120 sealingly bonded to proximal annular shelf 115 of body portion 110 at the proximal end of access assembly 100, and with outer sleeve 120 turned radially outwardly and extending proximally back onto itself at the distal end of access assembly 100, the fully enclosed, sealed chamber 122 is defined between outer sleeve 120 and body portion 110. As can be appreciated, in embodiments where chamber 122 is filed completely, or partially, with a compressible material, the compressible material may be inserted into chamber 122 prior to the sealing of chamber 122, e.g., prior to the bonding of free end 127 of outer sleeve 120 with proximal shelf 115 of body portion 110. Further, valve 130 (see FIG. 1) may be installed within outer sleeve 120 prior to, or after formation of chamber 122, to permit introduction of inflation fluids into chamber 122, as discussed above.

As can be appreciated, manufacturing and assembling access assembly 100 as described above is advantageous in that the manufacturing and assembling process is simplified and, thus, manufacturing costs are reduced. More specifically, since access assembly 100 is formed as a single component, less equipment and fewer manufacturing steps are needed, e.g., only a single type of mold need be provided to form access assembly 100, allowing the manufacture of access assembly 100 to be consistent, efficient and easily repeated. As a result, manufacturing costs are reduced and the likelihood of defect, e.g., due to insufficient engagement of components, is reduced. Further, requiring bonding (or welding) at only a single interface also reduces the complexity of the manufacturing process, the manufacturing costs, and the costs associated with testing the bond (or weld) of the access assembly 100.

Figure 12:
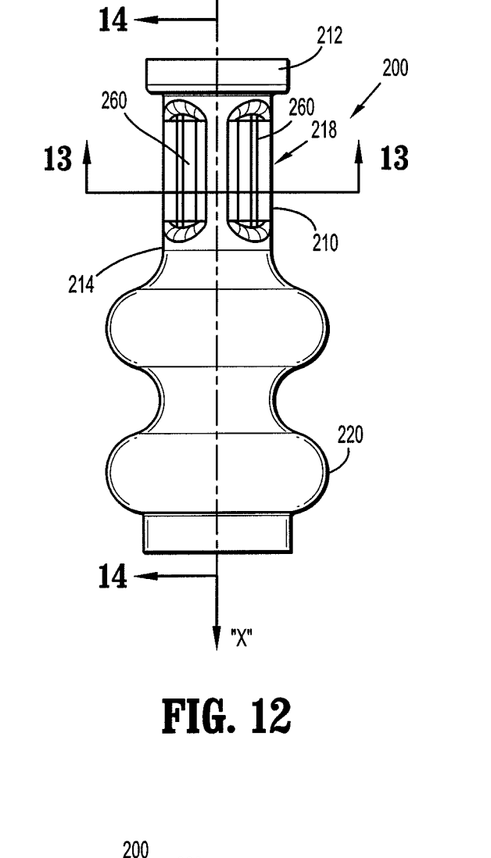
FIG. 12 is a side view of another embodiment of an access assembly in accordance with the present disclosure, the access assembly shown prior to assembly.
Figure 13:
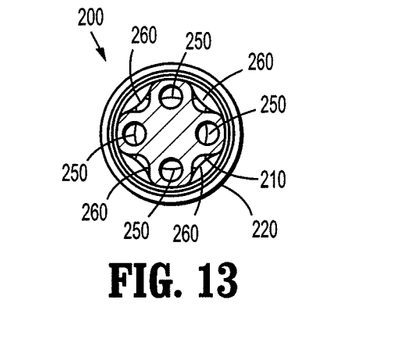
FIG. 13 is a transverse cross-sectional view of the access assembly of FIG. 12 taken along section line 13-13 of FIG. 12.
Figure 14:
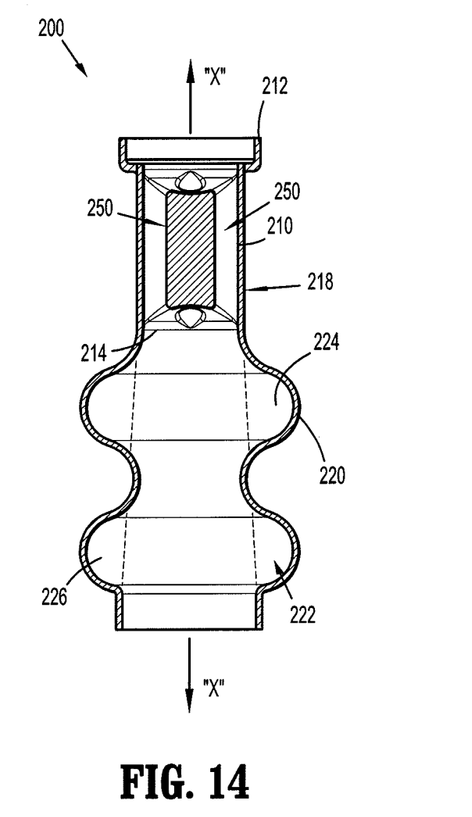
FIG. 14 is a longitudinal cross-sectional view of the access assembly of FIG. 12 taken along section line 14-14 of FIG. 12.

Referring now to FIGS. 12-14, another embodiment of an access assembly, access assembly 200, is shown. Access assembly 200 is similar to access assembly 100 and includes a generally cylindrical body portion 210 having an outer sleeve 220 that, when assembled, is radially positioned about body portion 210 to define a chamber 222 therebetween. In other words, when access assembly 200 is fully assembled, chamber 222 is radially disposed between body portion 210 and outer sleeve 220 and extends longitudinally between proximal rim 212 and distal rim 214 of body portion 210. As in the previous embodiment, due to the hourglass-shaped configuration of access assembly 200, chamber 222 is divided into proximal and distal ring-like sections 224, 226, respectively, that are selectively inflatable (either together or independently) to inflate access assembly 200.

With continued reference to FIGS. 12-14, body portion 210 of access assembly 200 includes a plurality, e.g., four (4), longitudinally extending lumens 250 defined therethrough. Lumens 250 of access assembly 200 extend completely through access assembly 200 and are expandable, due to the flexible configuration of body portion 210 of access assembly 200, to receive surgical instrumentation "S" (FIGS. 17-18) of varying size and/or configuration therethrough in sealing relation therewith. Further, each of the lumens 250 may have a substantially similar size and shape, or one or more lumens 250 may have a different size, shape and/or configuration. Additionally, one or more of lumens 250 may be biased toward a collapsed, or closed condition, wherein the openings extending through lumens 250 are closed, or sealed-off, inhibiting fluids from passing therethrough. As in the previous embodiment, lumens 250 may also include a protective lining (not shown) to prevent tearing of access assembly 200 as surgical instrumentation "S" (FIGS. 17-18) is inserted and manipulated therethrough and/or may be coated with a lubricant to assist in insertion and/or removal of surgical instrumentation "S" (FIGS. 17-18) therethrough.

Body portion 210 of access assembly 200 further includes a series of longitudinally extending indentations 260 defined within an outer surface 218 of body portion 210. As shown in FIGS. 12-13, four (4) indentations 260 are shown, although greater or fewer than four indentations 260 are contemplated. Indentations 260 extend longitudinally at least partially along body portion 210 of access assembly 200. As best shown in FIG. 13, an indentation 260 is positioned between each lumen 250 such that an alternating lumen/indentation arrangement circumferentially about body portion 210 is formed. However, it is also envisioned that multiple indentations 260 be provided between each lumen 250, or that the indentations 260 be positioned less frequently, e.g, between every two lumens 250. In the illustrated embodiment, both the four lumens 250 and the four indentations 260 are symmetrically positioned with respect to longitudinal axis "X-X" and are spaced 45 degrees relative to one another. However, as can be appreciated, the indentations 260 may be asymmetrically positioned with respect to one another and/or with respect to lumens 250.

Similar to slits 160 of access assembly 100 (FIG. 1), indentations 260 of access assembly 200 help increase the flexibility of access assembly 200 and also allow for increased maneuverability of surgical instrumentation "S" (FIGS. 17-18) inserted through lumens 250. Further, by providing indentations between each (or some) of the lumens 250 disposed through body portion 210, lumens 250 are capable of being flexed, or moved independently, or less dependently, of one another. In other words, indentations 260 allow for increased lateral manipulation of surgical instrumentation "S" (FIGS. 17-18) inserted therethrough, while reducing the effects on surgical instrumentation "S" (FIGS. 17-18) inserted through adjacent lumens 250. As such, indentations 260 may be further indented, e.g., to define a deeper configuration, or may be less indented, e.g., to define a more shallow configuration, according to the desired flexibility of access assembly 200 and/or the desired independence between lumens 250. Similarly, for accomplishing the same, indentations 260 may be configured to extend longitudinally along a substantial length of body portion 210 or, alternatively, may be configured to extend only partially along the length of body portion 210. Additionally, indentations 260 may define various transverse, cross-sectional profiles including arced, stepped, chevron, polygonal, or other configurations. Access assembly 200 may otherwise be configured similar to access assembly 100, discussed above.

Figure 15:
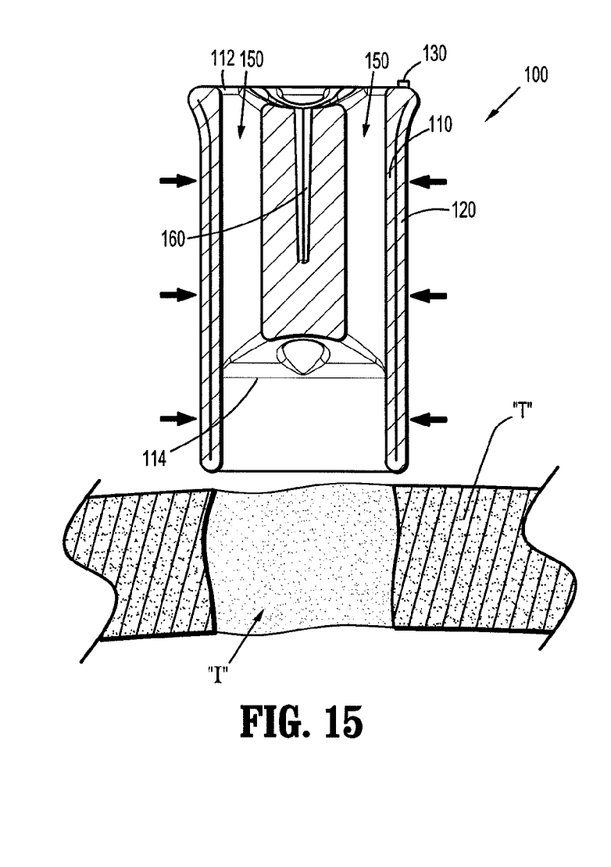
FIG. 15 is a longitudinal cross-sectional view of the access assembly of FIG. 1 shown in a deflated condition for positioning within an incision in tissue.
Figure 16:
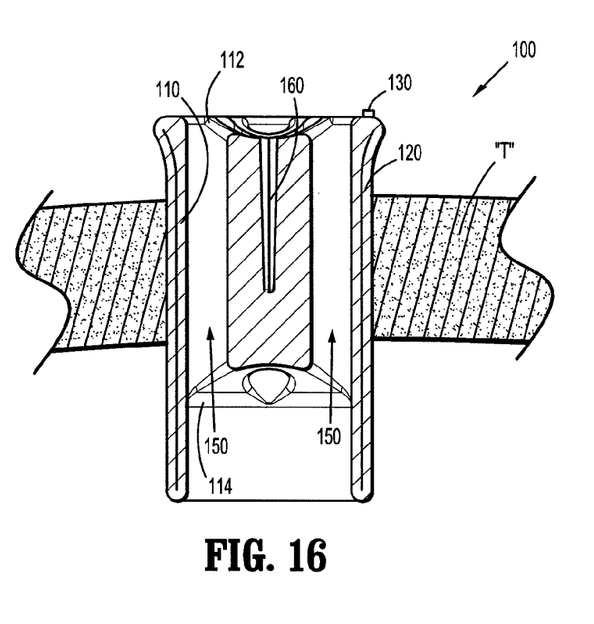
FIG. 16 is a longitudinal cross-sectional view of the access assembly of FIG. 1 shown in the deflated condition shown disposed through an incision in tissue.

With reference now to FIGS. 15-18, the use and operation of access assembly 100 will now be described. The use and operation of access assembly 200 is substantially similar to that of access assembly 100 and, thus, will not be repeated herein. Initially, as shown in FIG. 15, a single opening, or incision "I" is formed through a body tissue "T" to provide access to an underlying surgical site. Once incision "I" has been formed through body tissue "T," and with access assembly 100 in a deflated condition (FIG. 15), access assembly 100 is inserted through the incision "I" such that proximal rim 112 of body portion 110 and proximal section 124 of chamber 122 (see FIG. 18) are disposed on a proximal, or external side of tissue "T," while distal rim 114 of body portion 110 and distal section 126 of chamber 122 (see FIGS. 18) are disposed on a distal, or internal side of tissue "T," with waist 116 (FIG. 18) of body portion 110 disposed through the incision "I" in tissue "T." Such a positioning is facilitated by the hourglass configuration of access assembly 100, discussed above. As can be appreciated, with access assembly 100 in the deflated condition, as shown in FIGS. 15-16, access assembly 100 may be squeezed or compressed further, if necessary, to reduce access assembly 100 to a relatively smaller diameter for insertion through a relatively small incision "I." Likewise, in embodiments where chamber 122 is either partially, or entirely filled with a compressible material, access assembly 100 may be compressed, e.g., via a hand of the clinician, prior to being inserted into incision "I," to permit positioning therein.

Figure 17:
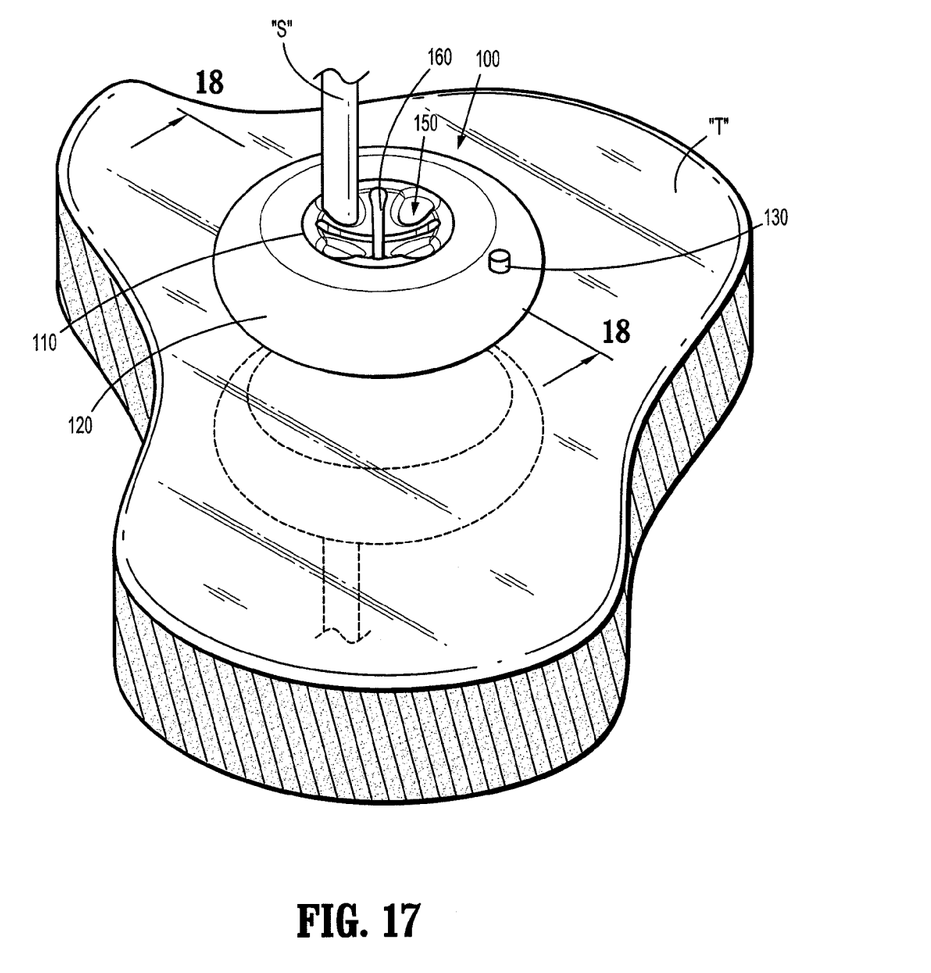
FIG. 17 is a top, perspective view of the access assembly of FIG. 1 shown disposed through an incision in tissue in an inflated condition with a surgical instrument disposed therethrough.
Figure 18:
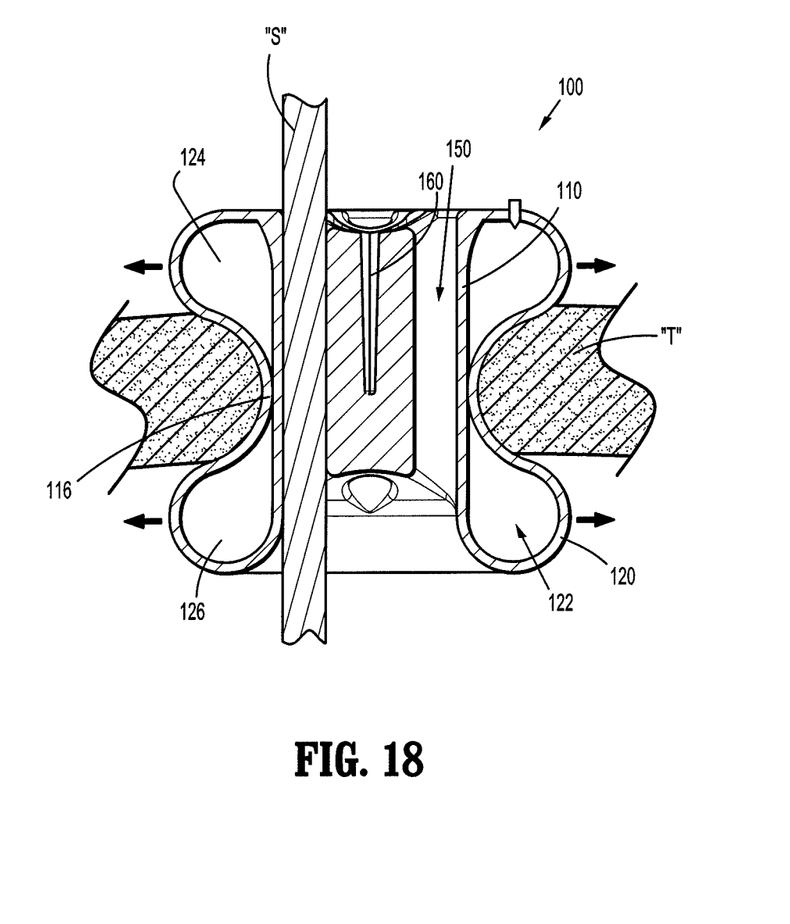
FIG. 18 is a longitudinal cross-sectional view of the access assembly of FIG. 1 taken along section line 18-18 of FIG. 17, the access assembly shown disposed through an incision in tissue in the inflated condition with a surgical instrument disposed therethrough.

Turning now to FIGS. 16-18, with access assembly 100 positioned within incision "I" in tissue "T," an inflation source (not shown) may be coupled to valve 130 for inflating chamber 122. As mentioned above, proximal and distal sections 124, 126, respectively, of chamber 122 may be inflated together, or may be inflated independently of one another. Further, chamber 122, or the sections 124, 126 thereof, may be inflated to a desired level such that sleeve 120 of access assembly 100 may be sealingly disposed through incision "I" (see FIG. 18) and/or such that access assembly 100 is retained in a substantially fixed position within the incision "I" in tissue "T." More particularly, the incision "I" is typically formed having a size that is greater than the diameter of access assembly 100 in the deflated condition, but smaller than the diameter of access assembly 100 in the fully inflated condition, such that, when chamber 122 is inflated, sleeve 120 of access assembly 100 is expanded radially outwardly toward tissue "T" to engage tissue "T" to form a substantially fluid-tight seal therebetween and/or to inhibit access assembly 100 from shifting or sliding within the incision "I" in tissue "T." As can be appreciated, the desired level of inflation of chamber 122 (or, individually, sections 124, 126) may depend on the size of the incision "I" in tissue "T," the anatomical location of the incision "I," the condition and/or composition of tissue "T," the necessity to maintain the position of surgical instrumentation "S" within the internal surgical site, the necessity to maintain an insufflated internal surgical site, or on other factors. In any configuration, the clinician may control the inflation level according to the desired parameters specific to the patient and/or the procedure, e.g., via a pressure gauge (not shown) of the inflation apparatus (not shown), such that access assembly 100 may be used in a wide range of procedures and patients.

In embodiments where a compressible material 127 is disposed within chamber 122, access assembly 100 may be released from the compressed condition once positioned within incision "I," allowing sleeve 120 to resiliently return toward its initial uncompressed state within incision "I," thereby retaining access assembly 100 in position. More particularly, as mentioned above, the incision "I" is typically formed having a size that is smaller than the diameter of access assembly 100 in the uncompressed state such that, when access assembly 100 is positioned within the incision "I" and is thereafter released, the resilient, or restoring feature of sleeve 120, e.g., due to the compressible material 127 disposed within chamber 122, urges access assembly 100 outwardly to engage tissue "T" on either side of access assembly 100 to form a substantially fluid-tight seal therebetween and/or to inhibit access assembly 100 from shifting or sliding within the incision "I" in tissue "T."

With access assembly 100 disposed within incision "I" in tissue "T" in fluid-tight sealing relation therewith and retained therein, surgical instrumentation "S" may be inserted through one (or more) of lumens 150 for carrying out a minimally-invasive surgical procedure within the internal surgical site. Alternatively, for procedures where insufflating the internal surgical site is necessary, an insufflation apparatus (not shown) may be disposed through one of lumens 150 to insufflate the surgical site prior to carrying out the surgical procedure. Due to the sealing relation between access assembly 100 and tissue "T" the insufflation of the surgical site can be maintained throughout the surgical procedure. More specifically, in such an embodiment, as mentioned above, lumens 150 may be biased toward a collapsed, or sealed condition such that insufflation fluids are inhibited from escaping the internal surgical site through lumens 150. Alternatively, surgical instrumentation "S," or stoppers (not shown) may be positioned within each of lumens 150 to maintain the substantially fluid-tight seal within the internal surgical site.

Turning now to FIGS. 17-18, with access assembly 100 in position within the incisions "I" in tissue "T," surgical instrumentation "S" may be inserted through one or more of lumens 150. As mentioned above, the manipulation of surgical instrumentation "S" within access assembly 100, e.g., to carry out a surgical procedure, is facilitated by the configuration of access assembly 100 and, more particularly, slits 160 (or indentations 260) defined within body portion 110 of access assembly 100. Thus, only a single access assembly 100 (requiring only a single incision) need be provided, even where the surgical procedure requires multiple instruments to be used independently or in conjunction with one another.

As can be appreciated, when the surgical procedure is complete, the surgical instrumentation "S" may be removed from access assembly 100 and access assembly 100 may be deflated (or compressed) back to the deflated condition (see FIGS. 15-16). Thereafter, access assembly 100 may be removed from the "I" in tissue "T."

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An access assembly, comprising:
a body portion defining a longitudinal axis and having at least one lumen defined therethrough and an indentation defined adjacent the at least one lumen, the at least one lumen configured for passage of a surgical instrument therethrough, the indentation configured to facilitate movement of the surgical instrument inserted through the at least one lumen; and
an outer sleeve disposed about the body portion to define a chamber therebetween, the chamber being selectively inflatable from a deflated condition, for positioning the access assembly within an opening in tissue, and an inflated condition, for retaining the access assembly within the opening in the tissue in sealing relation therewith, wherein the outer sleeve is monolithically formed and has proximal and distal ring-like sections and a waist, at least one of the proximal and distal ring-like sections having a first thickness and the waist having a second thickness different than the first thickness.

2. The access assembly according to claim 1, further comprising a valve disposed on the outer sleeve and in fluid communication with the chamber for selectively permitting introduction of inflation fluids into the chamber.

3. The access assembly according to claim 1, wherein a free end of the outer sleeve is sealingly engaged with the body portion to define the chamber therebetween.

4. The access assembly according to claim 1, wherein the access assembly defines a generally hourglass-shaped configuration.

5. The access assembly according to claim 1, wherein the chamber is configured for receipt of an inflation fluid therein.

6. The access assembly according to claim 1, wherein the chamber is at least partially filled with a compressible material.

7. The access assembly according to claim 1, wherein the first thickness is less than the second thickness.

8. The access assembly according to claim 1, wherein the indentation extends along a length of the body portion.

\* \* \* \* \*